US009421320B2

(12) United States Patent
Yokomizo et al.

(10) Patent No.: US 9,421,320 B2
(45) Date of Patent: Aug. 23, 2016

(54) BLOOD PROCESSING FILTER AND THE METHOD FOR MANUFACTURING THE SAME

(71) Applicant: ASAHI KASEI MEDICAL CO., LTD., Tokyo (JP)

(72) Inventors: Tomohisa Yokomizo, Tokyo (JP); Morikazu Miura, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 278 days.

(21) Appl. No.: 14/170,917

(22) Filed: Feb. 3, 2014

(65) Prior Publication Data

US 2014/0144832 A1 May 29, 2014

Related U.S. Application Data

(62) Division of application No. 13/237,029, filed on Sep. 20, 2011, now Pat. No. 8,881,914.

(60) Provisional application No. 61/427,327, filed on Dec. 27, 2010, provisional application No. 61/384,913, filed on Sep. 21, 2010.

(51) Int. Cl.
*A61M 1/38* (2006.01)
*A61M 1/36* (2006.01)
(Continued)

(52) U.S. Cl.
CPC .............. *A61M 1/38* (2013.01); *A61M 1/0218* (2014.02); *A61M 1/3633* (2013.01); *A61M 1/3636* (2014.02); *B01D 29/05* (2013.01); *A61M 2202/0439* (2013.01); *Y10T 29/49826* (2015.01); *Y10T 156/10* (2015.01)

(58) Field of Classification Search
None
See application file for complete search history.

(56) References Cited

U.S. PATENT DOCUMENTS

| 7,641,794 B2 * | 1/2010 | Oka ..................... A61M 1/3633 210/257.1 |
| 2003/0209479 A1 * | 11/2003 | Lynn ................... A61M 1/3633 210/257.1 |
| 2004/0251195 A1 | 12/2004 | Oka et al. | |

FOREIGN PATENT DOCUMENTS

| EP | 0526678 | 2/1993 |
| JP | 1-320064 | 12/1989 |
| JP | 7-267871 | 10/1995 |

(Continued)

OTHER PUBLICATIONS

Search report from E.P.O., mail date is Jan. 12, 2015.
(Continued)

*Primary Examiner* — Benjamin Kurtz
(74) *Attorney, Agent, or Firm* — Greenblum & Bernstein, P.L.C.

(57) ABSTRACT

This invention relates to a blood processing filter comprising a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element. The blood processing filter also includes a flow channel securing sheet arranged between the filter element and the outlet-side flexible container. A flow channel hole through which blood processed by the filter element passes is formed in the flow channel securing sheet. The outlet port is provided so as to be capable of communicating with the flow channel hole.

8 Claims, 11 Drawing Sheets

(51) Int. Cl.
    *A61M 1/02*    (2006.01)
    *B01D 29/05*    (2006.01)

(56) References Cited

FOREIGN PATENT DOCUMENTS

| | | |
|---|---|---|
| JP | 11-216179 | 8/1998 |
| JP | 2003-180822 | 7/2003 |
| JP | 2003-260111 | 9/2003 |
| JP | 2005-204781 | 8/2005 |
| JP | 2006-507881 | 3/2006 |
| JP | 2006-158738 | 6/2006 |
| JP | 2008-86352 | 4/2008 |
| JP | 2011-72814 | 4/2011 |
| KR | 10-0704335 | 4/2007 |
| WO | 90/15660 | 12/1990 |
| WO | 92/20428 | 11/1992 |
| WO | 95/17236 | 6/1995 |
| WO | 01/91880 | 12/2001 |
| WO | 02/04045 | 1/2002 |
| WO | 2004/050147 | 6/2004 |

OTHER PUBLICATIONS

Korea Office action, mail date is Apr. 2, 2014.
International Preliminary Report on Patentability for PCT/JP2011/071392, mailed Apr. 16, 2013.
Japan Office action, mail date is Dec. 10, 2013.
U.S. Appl. No. 13/237,061 to Tomohisa Yokomizo et al., filed Sep. 20, 2011.

\* cited by examiner

BLOOD PROCESSING FILTER AND THE METHOD FOR MANUFACTURING THE SAME

CROSS-REFERENCE RELATED APPLICATIONS

The present application is a division of U.S. application Ser. No. 13/237,029, filed Sep. 20, 2011, which is based on Provisional Application No. 61/427,327 filed Dec. 27, 2010 and Provisional Application No. 61/384,913 filed Sep. 21, 2010, the disclosures of which incorporated herein by reference in their entireties.

FIELD OF THE INVENTION

The present invention relates to a blood processing filter for removing undesirable components such as aggregates and leukocytes from blood. In particular, the present invention relates to a precise and disposable blood processing filter for removing microaggregates and leukocytes which may cause side effects from whole blood preparations, erythrocyte preparations, thrombocyte preparations, blood plasma preparations and the like for blood transfusion, as well as a method for manufacturing the blood processing filter.

RELATED BACKGROUND ART

It is becoming common for whole blood collected from a donor to be separated into blood component preparations such as an erythrocyte preparation, a thrombocyte preparation, and a blood plasma preparation and stored for transfusion. Since microaggregates and leukocytes included in these blood preparations cause various side effects during blood transfusion, the number of occasions for removing these undesirable components before blood transfusion has been increasing. The need for leukocyte removal has widely been recognized particularly in recent years. Legislation regarding removal of leukocytes from all kinds of blood preparations for blood transfusion before being used for transfusion has been introduced in an increasing number of countries.

The most common method of removing leukocytes from blood preparations is by processing blood preparations using a leukocyte removal filter. Conventionally, in many cases blood preparations processed using a leukocyte removal filter have been processed at the bedside when blood transfusion is performed. In recent years, however, to improve quality control of leukocyte-free preparations and efficiency of leukocyte removal operations, it is more common, particularly in developed countries, to process the blood preparations in blood centers before storing the blood preparations (pre-storage leukocyte removal).

A blood collection-separation set, typically consisting of two to four flexible bags, a tube connecting these bags, an anticoagulant, an erythrocyte preservation solution, a blood collection needle, and the like has been used for collecting blood from a donor, separating the blood into several blood components, and storing the blood components. A system in which a leukocyte removal filter is incorporated into such a blood collection-separation set has been widely used as an optimum system for the above-mentioned "pre-storage leukocyte removal". Such a system is called a "closed system" or an "integrated system" or the like. Such systems are disclosed in Japanese Patent Laid-Open No. 1-320064, International Publication No. WO 92/020428 and the like.

Conventionally, a filter element made from nonwoven fabric or a porous body packed in a hard container of polycarbonate or the like has been widely used as a leukocyte removal filter. However, because the container used in such a filter has a low level of air permeability, there is the problem that it is difficult to apply steam sterilization, which is widely used as a sterilization process in blood collection-separation sets. In one type of closed system, leukocytes are first removed from the whole blood preparation after collecting the blood. Subsequently, after the leukocyte removal filter is separated, the leukocyte-free blood is centrifuged for separation into various components. In another type of closed system, the whole blood is first centrifuged to be divided into various blood components, and then the leukocytes are removed. In the latter system, the leukocyte removal filter is also centrifuged together with the blood collection-separation set. At such time, a hard container may damage bags and tubes, or the hard container itself may not withstand the stress and may break during centrifugation.

To solve these problems, flexible leukocyte removal filters have been developed in which the container is made of a material having excellent flexibility and steam permeability that is the same as or similar to the material used for the bags of the blood collection-separation set. These flexible leukocyte removal filters that use a container made of a material having excellent flexibility and steam permeability are broadly classified into a type in which the filter element is welded to a sheet-like flexible frame, which is then welded to a housing material (see European Patent Specification EP 0526678 and Japanese Patent Laid-Open No. 11-216179), and a type in which a flexible container is directly welded to the filter element (see Japanese Patent Laid-Open No. 7-267871 and International Publication No. WO 95/17236). The former type may be hereinafter referred to as "frame welding type" and the latter may be referred to as "container welding type".

Normally, when processing blood with these types of leukocyte removal filters, a bag containing a blood preparation to be processed that is connected to a blood inlet side of the filter via a tube is placed at a height that is approximately 20 to 100 cm higher than the filter to allow the blood preparation to pass through the filter by the action of gravity. After filtration, the blood preparation is stored in a recovery bag that is connected to a blood outlet side of the filter via a tube. During filtration, a pressure loss occurs due to the resistance of the filter element, whereby the pressure in a space on the inlet side of the filter becomes a positive pressure. In the case of the filter that includes a flexible container, there is a tendency for the flexibility of the container itself to cause the container to swell like a balloon due to the positive pressure, thereby pressing the filter element against the container on the outlet side.

Furthermore, normally, a bag for storing blood that has been processed with the blood filter is placed at a position that is 50 to 100 cm lower than the filter, and blood moves through a channel on the downstream side due to the action of gravity. Hence, there is a tendency for the outlet side of the filter to become a negative pressure due to this action, and the flexible container is liable to adhere to the filter element.

That is, it has been pointed out previously that in the case of a filter that uses a flexible container, there is a problem that there is a strong tendency for the filter element to adhere to the outlet-side container due to a dual force, and as a result the flow of blood is obstructed and an adequate flow rate can not be obtained.

Various measures have been proposed to solve this problem. Representative examples of such measures include a method that inserts a soft polyvinyl chloride tube referred to as a "connecting rod" between the filter element and the outlet-side container to prevent adherence (see European Patent Specification EP 0526678), a method that prevents adherence by providing concavities and convexities with vertical intervals of 0.2 mm to 2 mm on the internal surface of a soft container (Japanese Patent Laid-Open No. 11-216179), and a method that inserts a screen made of knit fiber (International Publication No. WO 95/17236).

However, in a case in which a separate member such as a connecting rod or a screen is inserted, because it is required to perform welding precisely when welding the separate member to the container, there are the problems that a welding defect may occur, the manufacturing process is complicated, and the manufacturing cost is increased by the use of additional materials.

Furthermore, in the case of providing concavities and convexities on the internal surface of a container, there is the problem that the concavities and convexities on the internal surface of the container may induce a welding defect or may decrease the pressure resistance when the container material and the filter element are welded together.

Further, in a filter in which at least one of an inlet and an outlet is straddled and sealed by a second seal part, as disclosed in European Patent Specification EP 0526678, Japanese Patent Laid-Open No. 11-216179, and international Publication No. WO 04/050147, it is necessary to use a complicated tool or process used for sealing.

As described above, when the conventional technology is investigated from the point of view of a disadvantage caused by negative pressure that arises on the filter outlet side, in other words, from the point of view of how to secure a space that can serve as a passage for blood to pass through between the container and the filter element that are attempting to adhere to each other, it is found that the conventional technology is not necessarily satisfactory.

SUMMARY OF THE INVENTION

An object of the present invention is to provide a blood processing filter that, without leading to a risk of a welding defect, complicating the manufacturing process, or increasing costs, can avoid a situation in which a flow is inhibited and filtering performance is lowered due to adherence or the like between an outlet-side container and a filter element of a flexible filter, can effectively utilize the entire filter element, and can simultaneously achieve a high flow rate and high filtering performance.

To solve the above described problems, the inventors of the present invention carried out studies with respect to the effects of the shapes of flexible containers, filter elements and the like of blood processing filters and of the methods for assembling the blood processing filters, and succeeded in solving the above problems by providing a blood processing filter that can alleviate a decrease in a flow and a decline in leukocyte removal performance that are caused by adherence between an outlet-side container and a filter element that arises as a result of a negative pressure on a filter outlet side.

Specifically, the present invention relates to a blood processing filter including a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element; the blood processing filter further including a flow channel securing sheet that is arranged between the filter element and the outlet-side flexible container; wherein: a flow channel hole through which blood that is processed by the filter element passes is formed in the flow channel securing sheet, and the outlet port is provided so as to be capable of communicating with the flow channel hole. Note that, according to the present invention, the term "blood" includes blood preparations such as whole blood preparations, erythrocyte preparations, thrombocyte preparations and blood plasma preparations for blood transfusion. Further, according to the present invention, the term "capable of communicating" refers to, when a state in which blood is flowing is assumed, or when blood is actually flowing, a continuous empty space being formable in which adherence does not occur between an outlet-side flexible container and another element.

According to this blood processing filter, even if a dual force that is caused by a positive pressure on the inlet side and a negative pressure on the outlet side acts when filtering, a blood flow channel is secured between the flow channel hole in the flow channel securing sheet and the outlet port. Accordingly, a situation in which a blood flow is inhibited and filtering performance is lowered due to adherence or the like between the outlet-side flexible container and the filter element of the blood processing filter is avoided, the configuration is advantageous in terms of effectively utilizing the entire filter element, and a high filtering flow rate and high filtering performance can both be achieved in a compatible manner.

The above described blood processing filter can further include: a first seal part that seals the inlet-side flexible container and the filter element in a band shape, and that is provided so as to surround the inlet port; and an annular second seal part that seals at least the inlet-side flexible container and the outlet-side flexible container, and that is provided so as to surround the first seal part at a position that is closer to an outer edge than the first seal part; wherein a valley part corresponding to the first seal part is provided on an outlet side of the filter element, and at least one portion of the flow channel hole that is formed in the flow channel securing sheet is arranged in an empty space region that is formed by the valley part in a state in which blood is flowing.

The present invention can also provide a blood processing filter according to above described blood processing filter, in which a plurality of flow channel holes are formed in the flow channel securing sheet, and at least one portion of all of the flow channel holes is arranged in the empty space region that is formed by the valley part.

Further, the present invention can provide a blood processing filter according to above described blood processing filter, in which an outlet opening that communicates with an inside of the outlet-side flexible container is formed in the outlet port, and at least one portion of the outlet opening is arranged so as to overlap with at least one of the flow channel hole and the valley part.

The present invention can also provide a blood processing filter according to above described blood processing filter, in which the second seal part sandwiches and adheres the flow channel securing sheet between the inlet-side flexible container and the outlet-side flexible container.

Further, the present invention can provide a blood processing filter according to above described blood processing filter, in which the first seal part sandwiches and adheres the filter element between the inlet-side flexible container and the flow channel securing sheet.

Furthermore, the present invention can provide a blood processing filter according to the above described blood processing filter, in which the second seal part sandwiches and adheres the flow channel securing sheet between the inlet-side flexible container and the outlet-side flexible container, and the first seal part sandwiches and adheres the filter element between the inlet-side flexible container and the flow channel securing sheet.

In addition, the present invention can provide a blood processing filter according to the above described blood processing filter, in which the flow channel securing sheet is arranged so as to cover an effective filtering portion of the filter element, and a plurality of the flow channel holes are formed in the flow channel securing sheet in a region that faces the effective filtering portion.

The present invention can also provide a blood processing filter according to the above described blood processing filter in which, in the flow channel securing sheet, a proportion of a gross area of the flow channel holes with respect to an area of the effective filtering portion is between 30% and 99%.

Further, the present invention can provide a blood processing filter according to the above described blood processing filter, in which a thickness of the flow channel securing sheet is between 0.1 mm and 3 mm.

Furthermore, the present invention can provide a blood processing filter according to the above described blood processing filter, in which a thickness of the flow channel securing sheet is between 0.2 mm and 2 mm.

Further, the present invention can provide a blood processing filter according to the above described blood processing filter, in which a thickness of the flow channel securing sheet is between 0.2 mm and 1.5 mm.

In addition, the present invention can provide a blood processing filter according to the above described blood processing filter, in which the flow channel hole of the flow channel securing sheet is a slit shape, and a width of the flow channel hole is between 0.5 mm and 20 mm.

Further, the present invention can provide a blood processing filter according to the above described blood processing filter, in which the flow channel hole of the flow channel securing sheet is a slit shape, and a width of the flow channel hole is between 1 mm and 15 mm.

Furthermore, the present invention can provide a blood processing filter according to the above described blood processing filter, in which the flow channel hole of the flow channel securing sheet is a slit shape, and a width of the flow channel hole is between 1 mm and 10 mm.

In addition, the present invention can provide a blood processing filter according to the above described blood processing filter, that includes: a frame sheet that is arranged between the filter element and the inlet-side flexible container; a first seal part that, in a state in which the filter element is clamped by the frame sheet and the flow channel securing sheet, seals the frame sheet, the filter element, and the flow channel securing sheet in a band shape, and that is provided in a ring shape along a periphery of the filter element; and an opening that is formed on an inner side that is surrounded by the first seal part, of the frame sheet.

Further, the present invention can provide a blood processing filter according to the above described blood processing filter, that includes a valley part that is provided in correspondence to the first seal part on an outlet side of the filter element, wherein at least one portion of the flow channel hole formed in the flow channel securing sheet is arranged in an empty space region that is formed by the valley part in a state in which blood is flowing.

Furthermore, the present invention can provide a blood processing filter according to the above described blood processing filter, in which a plurality of the flow channel holes are formed in the flow channel securing sheet, and at least one portion of all of the flow channel holes is arranged in the empty space region that is formed by the valley part.

The present invention also relates to a method for manufacturing a blood processing filter that includes a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element; the method including: an installing step of arranging the inlet-side flexible container and the outlet-side flexible container so as to sandwich the filter element, and arranging a flow channel securing sheet in which a flow channel hole is formed through which blood processed by the filter element passes, between the filter element and the outlet-side flexible container; and a sealing step of sealing the inlet-side flexible container and the outlet-side flexible container in a state in which the filter element and the flow channel securing sheet are arranged at predetermined positions in the installing step; wherein, in the installing step, the outlet port is arranged at a position at which the outlet port is capable of communicating with the flow channel hole of the flow channel securing sheet.

Further, the present invention can provide a method for manufacturing a blood processing filter according to the above described method, wherein: the sealing step includes a first sealing step of forming a first seal part that seals the inlet-side flexible container, the filter element, and the flow channel securing sheet in a band shape so as to surround an area where the inlet port is formed, without adhering the filter element and the outlet-side flexible container, and a second sealing step of sealing to form an annular second seal part so as to surround the first seal part at a position that is closer to an outer edge than the first seal part; a band-shaped valley part corresponding to the first seal part is generated on an outlet side of the filter element by the first sealing step; and in the installing step, the flow channel securing sheet is arranged so that at least one portion of the flow channel hole formed in the flow channel securing sheet is arranged in an empty space region that is formed by the valley part in a state in which blood is flowing.

Furthermore, the present invention can provide a method for manufacturing a blood processing filter according to the above described method, in which an outlet opening that communicates with an inside of the outlet-side flexible container is formed in the outlet port, and in the installing step, at least one portion of the outlet opening is arranged so as to overlap with at least one of the flow channel hole and the valley part.

Further, the present invention can provide a method for manufacturing a blood processing filter according to the above described method, in which, in the second sealing step, the flow channel securing sheet is sandwiched and adhered between the inlet-side flexible container and the outlet-side flexible container, and in the first sealing step, the filter element is sandwiched and adhered between the inlet-side flexible container and the flow channel securing sheet.

DESCRIPTION OF THE PREFERRED EMBODIMENTS

Embodiments of the present invention are described hereunder with reference to the drawings. Note that the term "blood" that is described in each of the following embodiments includes blood preparations such as whole blood preparations, erythrocyte preparations, thrombocyte preparations and blood plasma preparations for blood transfusion. Further, although various forms can be adopted for the external shape of the blood processing filter, such as a rectangular shape, a disc shape, an oval disc shape, and an elliptical shape, a rectangular shape is preferable for decreasing loss of materials when the filters are manufactured. Accordingly, in the following embodiments, an example in which the blood processing filter has a rectangular shape is described.

Figure 1:
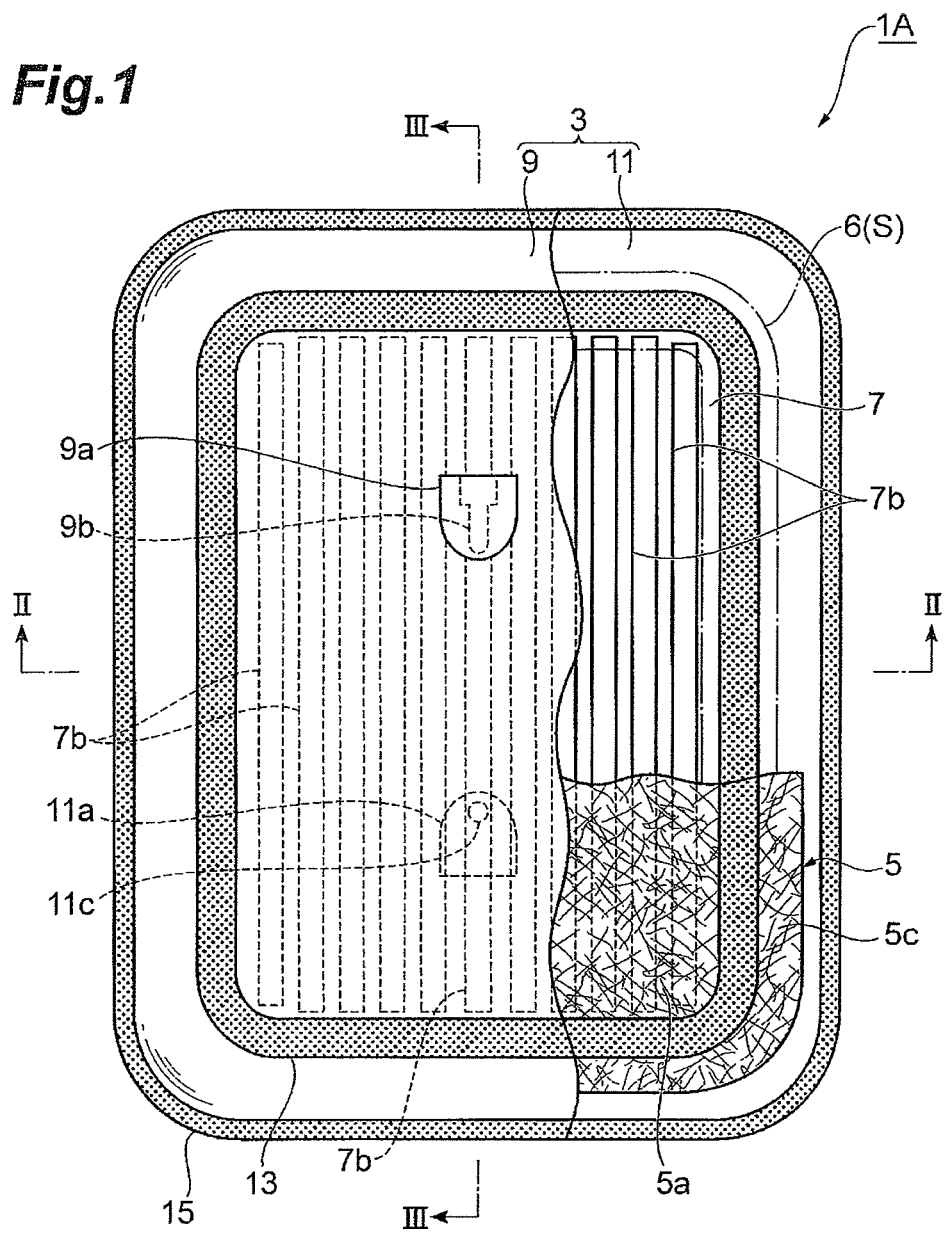
FIG. 1 is a plan view that illustrates one portion of a blood processing filter according to a first embodiment of the present invention, that is shown in a cut-away manner.
Figure 2:
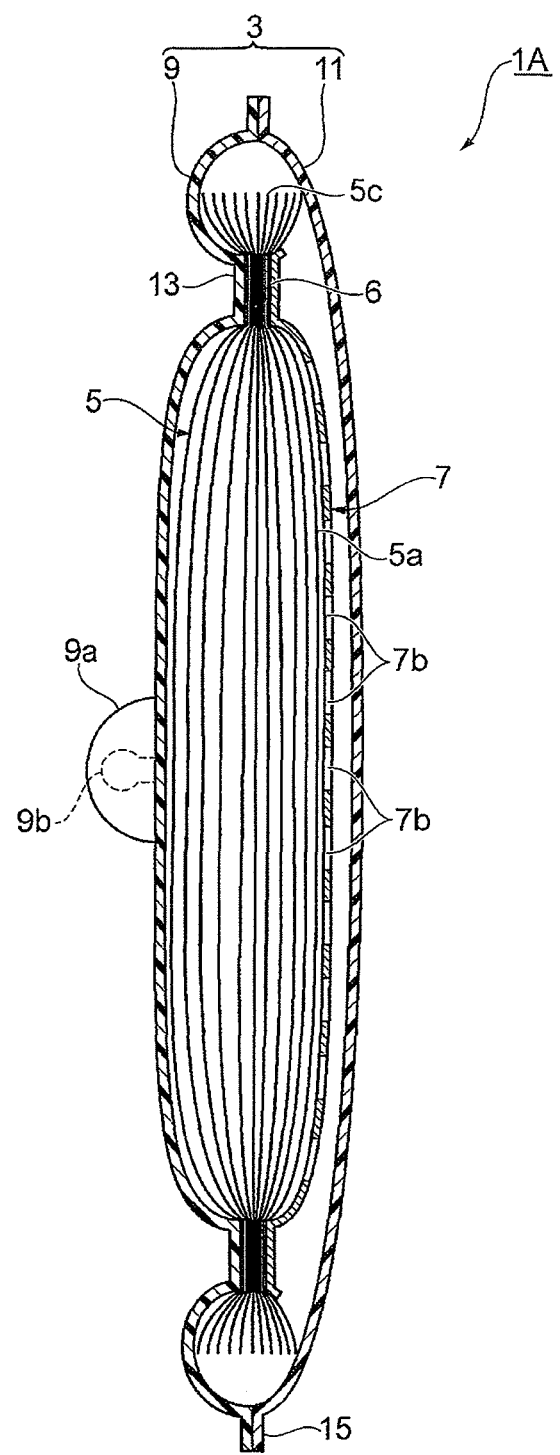
FIG. 2 is a sectional view taken along a line II-II in FIG. 1.
Figure 3:
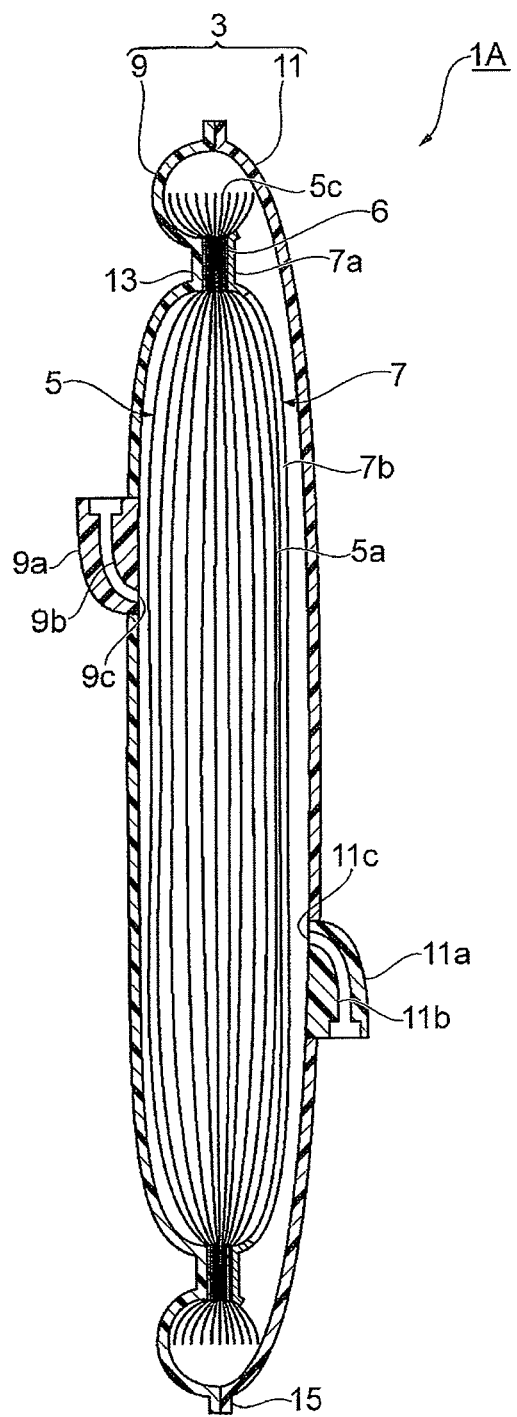
FIG. 3 is a sectional view taken along a line III-III in FIG. 1.

First, a blood processing filter 1A relating to a first embodiment of the present invention is described referring to FIGS. 1 to 3. The blood processing filter 1A includes a flexible container 3 having an inlet port 9a and an outlet port 11a for blood, a sheet-like filter element 5 that is arranged so as to divide the inside of the flexible container 3 into an inlet port 9a side and an outlet port 11a side, and a flow channel securing sheet 7 that is arranged in an overlapping manner with respect to the filter element 5.

The flexible container 3 has a rectangular, flat shape. Here, the term "flat shape" means a shape having a thin thickness and a wide surface. The flexible container 3 includes an inlet-side container 9 that has a rectangular sheet shape, and an outlet-side container 11 that has a rectangular sheet shape. An inlet port 9a in which an inlet flow channel 9b that allows the inside and the outside to communicate is formed is sealed in the inlet-side container 9. An outlet port 11a in which an outlet flow channel 11b that allows the inside and the outside to communicate is formed is sealed in the outlet-side container 11. In this connection, as used herein, the term "seal (to seal)" refers to fixing by bonding (including welding) to a degree that can prevent leakage of a liquid. Further, the inlet-side container 9 is an example of an inlet-side flexible container, and the outlet-side container 11 is an example of an outlet-side flexible container.

The inlet-side container 9 and the outlet-side container 11 overlap with each other through the rectangular filter element 5 and the rectangular flow channel securing sheet 7. The inlet-side container 9 is sealed along the periphery of the filter element 5 in a state in which the filter element 5 is clamped between the inlet-side container 9 and the flow channel securing sheet 7. A band-shaped bonding region along the periphery of the filter element 5 is an inside seal part 13. The inside seal part 13 surrounds the inlet port 9a in a rectangular ring shape. An inner region that is further on the inside than the inside seal part 13 is a filtering region through which blood flows. A portion of the filter element 5 that faces the filtering region is an effective filtering portion 5a. In this connection, a protruding nonwoven fabric portion 5c that is a surplus portion of the filter element 5 protrudes to the outside of the inside seal part 13 within the flexible container 3. The inside seal part 13 corresponds to a first seal part.

Figure 4:
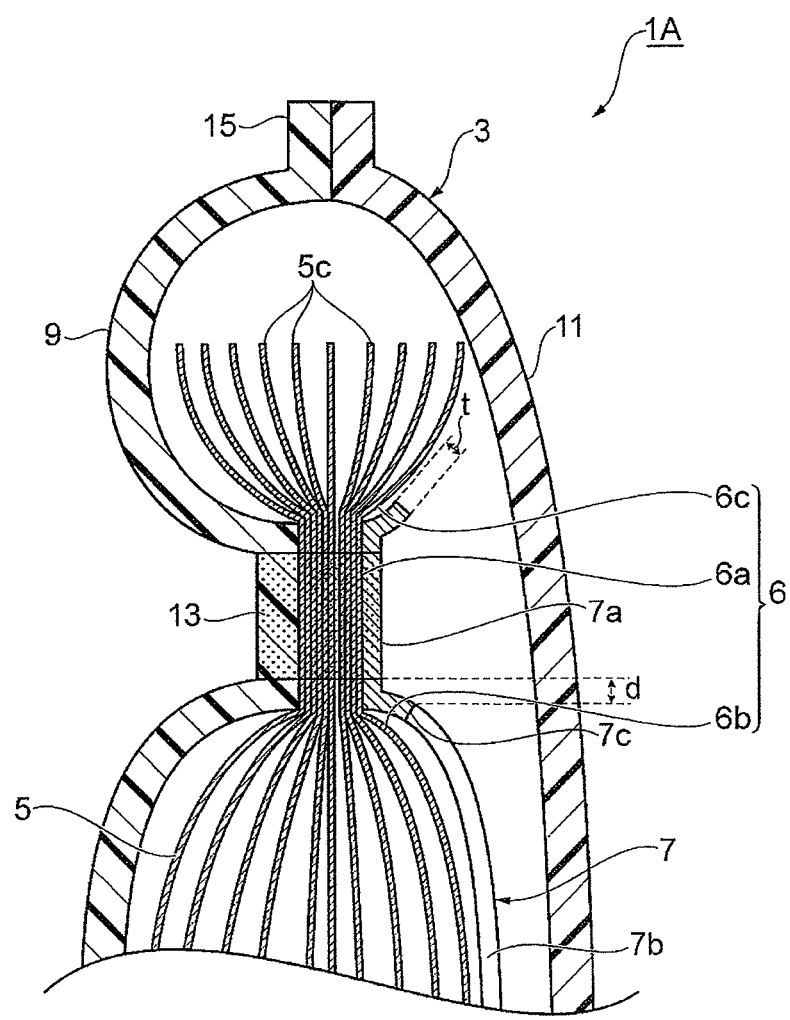
FIG. 4 is a sectional view that illustrates, in an enlarged manner, an end of a flow channel hole of a flow channel securing sheet and an inside seal part.

On the outlet side of the filter element 5, that is, on the rear side of the filter element 5, a rectangular ring shaped recess is formed in correspondence to the rectangular ring-shaped inside seal part 13 (see FIG. 4). This recess is formed as a result of the filter element 5 being sandwiched and compressed by the inlet-side container 9 and the flow channel securing sheet 7 and being adhered in that state. This recess is a valley part 6 that is provided on the outlet side of the filter element 5.

The peripheries of the inlet-side container 9 and the outlet-side container 11 are sealed together in a mutually overlapping manner so as to surround the inside seal part 13 in a ring shape at a position that is closer to an outer edge than the inside seal part 13. The band-shaped bonding region in which the inlet-side container 9 and the outlet-side container 11 are directly bonded is an outside seal part 15. The outside seal part 15 corresponds to a second seal part.

The flow channel securing sheet 7 is also sealed to the filter element 5 at the inside seal part 13. Accordingly, a recess 7a that is formed in the same shape as the valley part 6 of the filter element 5 also arises in the flow channel securing sheet 7. The outlet-side container 11 is not bonded to the filter element 5 and the flow channel securing sheet 7. In an at-rest state, the outlet-side container 11 is in a state in which the outlet-side container 11 is roughly separated from the valley part 6 of the filter element 5 and the recess 7a of the flow channel securing sheet 7. If a state is assumed in which blood is flowing (a negative pressure state), an empty space region (hereunder, referred to as a "passage region") S is formed between the filter element 5 and the outlet-side container 11 by the valley part 6 of the filter element 5 and the recess 7a of the flow channel securing sheet 7 (see FIG. 8).

Figure 5:
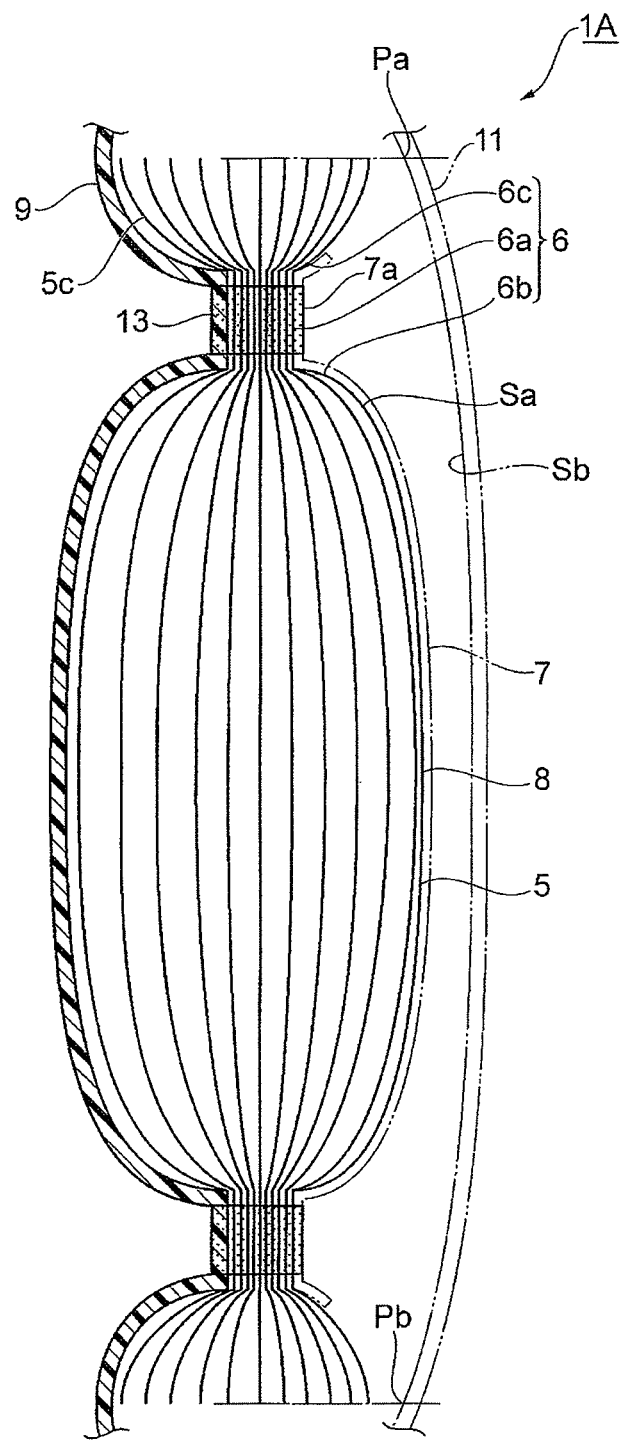
FIG. 5 is a view that schematically illustrates a relationship between a portion corresponding to a valley part of a filter element and another portion.

The valley part 6 of the filter element 5 will now be described in further detail referring to FIG. 5. FIG. 5 is a schematic view that illustrates the filter element 5 in an at-rest state, that is, a state in which blood is not flowing. In particular, FIG. 5 is a view that schematically illustrates the relationship between an area in which the valley part 6 is formed and other areas. The valley part 6 includes a bottom part 6a that overlaps with the inside seal part 13, an inner slanted face portion 6b that rises towards the inside of the inside seal part 13 from the bottom part 6a, and an outer slanted face portion 6c that rises towards the outside of the inside seal part 13. The inner slanted face portion 6b smoothly connects to a main region portion 8 on the outlet side of the filter element 5. The outer slanted face portion 6c is a region that is formed by the protruding nonwoven fabric portion 5c.

Formation of the valley part 6 will now be described in detail. A laminated filter element has a constant thickness, and the surface of the filter element is in a flat state when a process such as welding has not been performed. Subsequently, for example, if the two faces of the filter element are sandwiched with a PVC sheet and high frequency welding is performed, the welded place is crushed in the welding process, and the welded place becomes thin in comparison to the original thickness of the filter element. In this case, according to the filter element 5 of the present embodiment, for example, high frequency welding is carried out using a predetermined mold to form the inside seal part 13, and as a result an annular welded place is formed. Although the places other than the welded place are substantially flat over the entire area of the filter element 5 after welding also, only the vicinity of the welded place is different, and when attention is focused on the outlet side it can be seen that a place adjoining the welded place rises almost perpendicularly from the welded place and connects to a flat portion (main region portion 8) of the filter element 5. More specifically, the region corresponding to the welded place is the bottom part 6a of the valley part 6, the region that rises almost perpendicularly towards the inner side from the bottom part 6a is the inner slanted face portion 6b, and the region that rises almost perpendicularly towards the outer side from the bottom part 6a is the outer slanted face portion 6c.

Next, the relationship between a face on the outlet side of the filter element 5 on which the valley part 6 is formed (hereunder, referred to as "outlet-side nonwoven fabric surface") and the outlet-side container 11 is described. First, a cross section (hereunder, referred to as "hypothetical cross section") that cuts the blood processing filter 1A along an arbitrary straight line that passes through approximately the center of the outlet-side nonwoven fabric surface is supposed. FIG. 5 is a view that schematically illustrates the hypothetical cross section.

In this case, a first line segment Sa that indicates the outlet-side nonwoven fabric surface on the hypothetical cross section, and a second line segment Sb that indicates a region which corresponds to the outlet-side nonwoven fabric surface among the entire inner surface of the outlet-side container 11 on the hypothetical cross section are specified. The first line segment Sa links both ends of the outlet-side nonwoven fabric surface and is formed in the same shape as the outlet-side nonwoven fabric surface. With respect to the second line segment Sb, first, an orthogonal direction to the longitudinal direction of the filter element 5 on the hypothetical cross section is assumed to be a corresponding direction, and a straight line that extends along the respective corresponding directions from both ends of the outlet-side nonwoven fabric surface is assumed. Next, two points Pa and Pb at which the two straight lines intersect with the inner surface of the outlet-side container 11 are specified. The two points Pa and Pb correspond to both ends of the outlet-side nonwoven fabric surface on the inner surface of the outlet-side container 11. A line segment that links the two points Pa and Pb in a manner that follows the shape of the inner surface of the outlet-side container 11 is the second line segment Sb.

Comparing the first line segment Sa and the second line segment Sb, since the valley part 6 is formed in the filter element 5, the first line segment Sa is longer than the second line segment Sb. As a result an empty space region is formed in the valley part 6 in an at-rest state. Further, with respect to the outlet-side container 11, although the material thereof has some margin for expansion and contraction it is not a material that expands by any amount, and since the first line segment Sa is longer than the second line segment Sb, even if a state is entered in which blood flows and is attached thereto (is attached due to a negative pressure), the outlet-side container 11 does not contact the filter element 5 in the vicinity of the inside seal part 13, in particular in the vicinity of the bottom part 6a of the valley part 6. As a result, the passage region S is formed which can be used as a flow channel for blood.

As shown in FIGS. 1 to 4, the flow channel securing sheet 7 is arranged so as to cover the effective filtering portion 5a of the filter element 5 on the outlet side of the filter element 5. A plurality of flow channel holes 7b are formed in a region facing the effective filtering portion 5a of the flow channel securing sheet 7. The outlet port 11a of the outlet-side container 11 is arranged so as to be capable of communicating with a flow channel hole 7b. In this connection, the statement "the outlet port 11a is arranged so as to be capable of communicating with a flow channel hole 7b" means that, when a state in which blood is flowing is assumed, or when blood is actually flowing, it is possible to form a continuous empty space which is not adhered between the outlet-side container 11 and another element, and for example, includes a case in which the outlet port 11a is arranged so as to overlap with the flow channel hole 7b or the valley part 6 in an at-rest state, or a case in which, when blood is flowing, the outlet port 11a is arranged in the passage region S formed by the valley part 6. According to the present embodiment, the outlet port 11a is arranged so as to overlap with the valley part 6 in an at-rest state. As a result, in a state in which blood is flowing, a forms is realized in which a continuous empty space is formed from the outlet port 11a to the passage region S.

Figure 6:
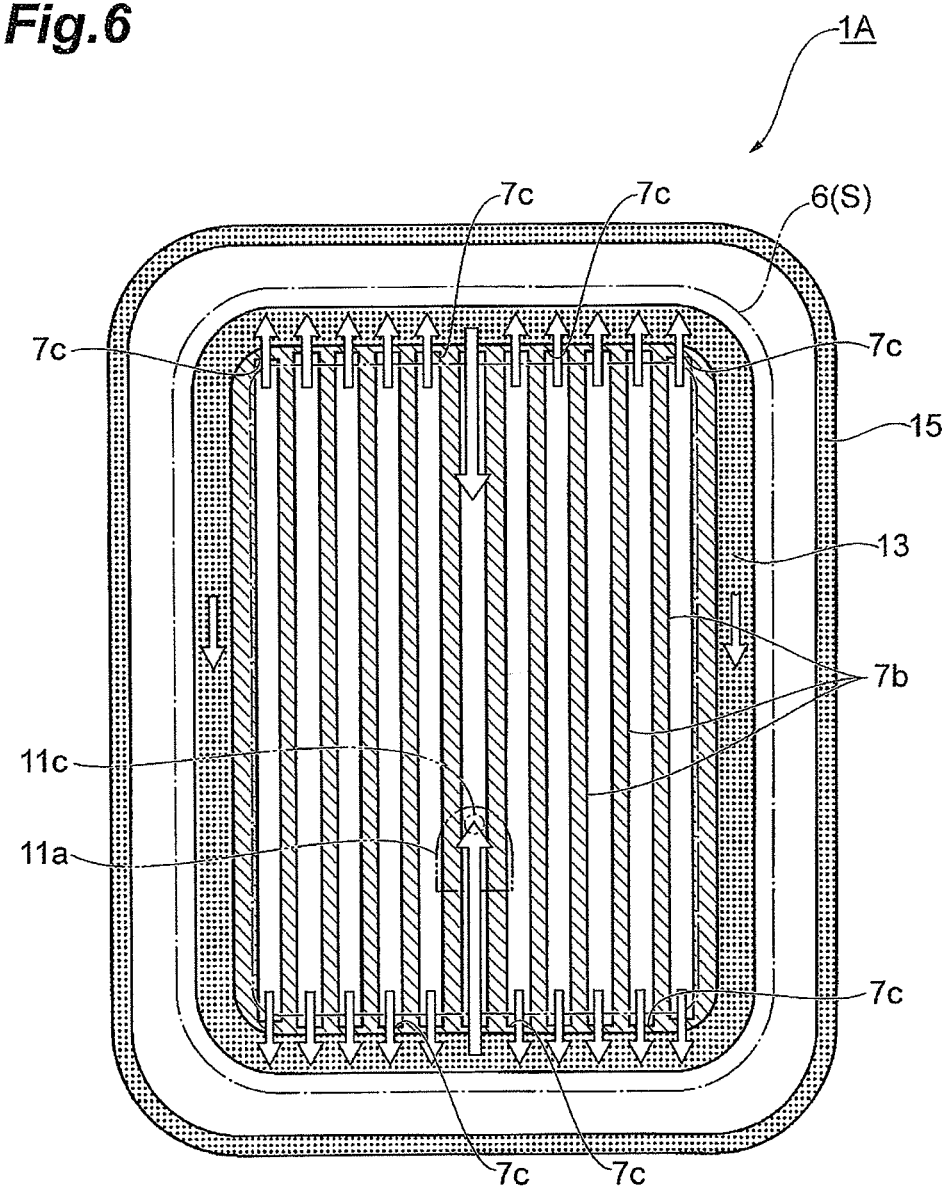
FIG. 6 is a view that schematically illustrates a flow of blood inside an outlet-side container.

With respect to all of the plurality of flow channel holes 7b formed in the flow channel securing sheet 7, at least a portion of the flow channel holes 7b is arranged over the inner slanted face portion 6b. Further, when a state in which blood is flowing is assumed, a state is entered in which at least a portion of the flow channel holes 7b is arranged in the passage region S as described later. As a result, the respective flow channel holes 7b connect to each other so that blood can freely enter and leave through the passage region S in a state in which blood is flowing, and thus the inflow and outflow of blood are stably maintained (see FIG. 6).

Specifically, the plurality of flow channel holes 7b are formed in the flow channel securing sheet 7 by partially cutting out the sheet. Each flow channel hole 7b is formed in a slit shape that is long along the longitudinal direction of the flow channel securing sheet 7. Hereunder, the slit-shaped flow channel holes 7b are also referred to as "slit portions". The plurality of slit portions 7b and sheet portions that remain between adjoining slit portions 7b are arranged so as to face the effective filtering portion 5a. Preferably, in the flow channel securing sheet 7, the proportion of the gross area of the slit portions (flow channel holes) 7b with respect to the area of the effective filtering portion 5a of the filter element 5 is between 30% and 99%.

Two ends 7c of the slit portions 7b extend as far as the vicinity of the inside seal part 13. As a result, the two ends 7c of the slit portions 7b are arranged over the inner slanted face portion 6b of the valley part 6. Further, when a state in which blood is flowing is assumed, a state is entered in which the two ends 7c of the slit portions 7b are arranged in the passage region S. By at least one portion of the slit portions 7b being arranged in the passage region S, a state is entered in which the inside of the slit portions 7b and the inside of the passage region S communicate, and thus a blood flow channel is formed.

From the viewpoint of stably maintaining the blood flow, it does not matter how close the ends 7c of the slit portions 7b are to the inside seal part 13, that is, it does not matter how large an area is in which at least one portion of the slit portions 7b is arranged in the passage region S. However, if a portion of the slit portion 7b rests on (overlaps with) the inside seal part 13, the slit portion 7b may hinder formation of the inside seal part 13. Therefore, it is good for a distance d (see FIG. 4) between the end 7c of each slit portion 7b and an inside end of the inside seal part 13 to be between 0.1 mm and 3 mm, preferably between 0.3 mm and 2 mm, and more preferably between 0.5 mm and 1.5 mm.

The size of the slit portions 7b can be decided in various ways. From the viewpoint of blood flow, the larger the gross area of the slit portions 7b is, the larger the size of a blood flow channel that can be secured will be. However, if each individual slit portion 7b is too large, there is a concern that the filter element 5 and the outlet-side container 11 will contact inside the slit portions 7b due to deformation of the outlet-side container 11 that is caused by a negative pressure, and that the blood flow channel will be blocked. Accordingly, it is preferable that the width of each slit portion 7b is such that blockage of the flow channel does not occur. For example, although the width will also be influenced by the softness of the outlet-side container 11 that depends on the material and thickness and the like of the outlet-side container 11, it is good for the width of the slit portions 7b to be between 0.5 mm and 20 mm, preferably between 1 mm and 15 mm, and more preferably between 1 mm and 10 mm.

An interval between one slit portion 7b and another slit portion 7b is not particularly limited as long as it is possible to maintain the shape of the slit portions 7b during the manufacturing process, during use of the blood processing filter 1A, and during the transportation process, and to also obtain an adequate strength. The smaller a value is for the interval between the slit portions 7b, the larger the gross area of the slit portions 7b can be.

Normally, a thickness t of the flow channel securing sheet 7 can be substantially the same as that of the flexible container 3. Even if the width of the slit portions 7b is the same, the greater the thickness of the flow channel securing sheet 7 is, the greater the size of the flow channel that can be secured, and the greater the decrease in the risk of the flow channel being blocked due to deformation of the outlet-side container 11. However, as the thickness of the flow channel securing sheet 7 increases, the greater a qualitative increase in a loss amount becomes due to an increase in the space inside the slit portions 7b. A thickness between 0.1 mm and 3 mm is good as the thickness t of the flow channel securing sheet 7, and preferably the thickness t is between 0.2 mm and 2 mm, and more preferably between 0.2 mm and 1.5 mm.

The inlet port 9a that is sealed in the inlet-side container 9 can be appropriately arranged in a region on the inside of the inside seal part 13. The inlet port 9a according to the present embodiment is arranged at one end side in the longitudinal direction of the flexible container 3, that is, on the upper side in a state in which the blood processing filter 1A is placed upright for blood processing. An inlet flow channel 9b that accepts pre-processing blood when an inlet-side circuit 102 (see FIG. 7) through which blood flows is formed, is formed in the inlet port 9a. An inlet opening 9c is formed in the inlet port 9a. The inlet opening 9c allows the inlet flow channel 9b and the inside of the inlet-side container 9 to communicate.

The outlet port 11a that is sealed in the outlet-side container 11 can be appropriately arranged in a region on the inside of the outside seal part 15. The outlet port 11a according to the present embodiment is arranged at the other end side in the longitudinal direction of the flexible container 3, that is, on the lower side in a state in which the blood processing filter 1A is placed upright for blood processing. An outlet flow channel 11b that discharges blood that is processed by the filter element 5 when an outlet-side circuit 104 (see FIG. 7) through which blood flows is formed, is formed in the outlet port 11a.

An outlet opening 11c is formed in the outlet port 11a. The outlet opening 11c allows the inside of the outlet-side container 11 and the outlet flow channel 11b to communicate. At least one portion of the outlet opening 11c of the outlet port 11a is arranged so as to overlap in a planar view with the slit portions 7b of the flow channel securing sheet 7. By arranging the outlet opening 11c so that at least one portion thereof overlaps with the slit portions 7b, blood flows efficiently and the filter element 5 as a filter material can be effectively utilized.

Specifically, in a state in which blood is flowing, a negative pressure arises on the outlet side of the filter element 5 and a force acts on the outlet-side container 11 to cause the outlet-side container 11 to stick to the filter element 5 side. However, on the outlet side of the filter element 5, the valley part 6 is recessed with respect to the main region portion 8 (see FIG. 5) and, in addition, the outer slanted face portion 6c (protruding nonwoven fabric portion 5c) of the valley part 6 interferes with the outlet-side container 11 so that adherence to the flow channel securing sheet 7 or the filter element 5 is restricted, and therefore an empty space region (passage region) S is formed by the valley part 6 between the filter element 5 and the outlet-side container 11. One part of the slit portions 7b of the flow channel securing sheet 7 is arranged over the inner slanted face portion 6b of the valley part 6. In a state in which blood is flowing, the slit portions 7b connect as a blood flow channel to the passage region S, and furthermore this blood flow channel and the outlet opening 11c of the outlet port 11a are connected as a blood flow channel. As a result, blood processed by the filter element 5 can be efficiently discharged to outside the blood processing filter 1A, and at the same time the possibility of the outlet opening 11c being blocked by the filter element 5 can be avoided.

In this connection, although at least one portion of the outlet opening 11c according to the present embodiment is arranged so as to overlap with the slit portions 7b, a form may also be adopted in which a similar effect is obtained by arranging at least one portion of the outlet opening 11c so as to overlap with the passage region S in a planar view.

According to the blood processing filter 1A as described above, the outlet-side container 11 is not included in the inside seal part 13. As a result, the passage region S is formed by the valley part 6 of the filter element 5, and the passage region S is utilized as a blood flow channel. The slit portions (flow channel holes) 7b of the flow channel securing sheet 7 connect as a blood flow channel to the passage region S that surrounds the effective filtering portion 5a of the filter element 5, and discharge blood to the outlet port 11a.

That is, on the outlet side, the flow of blood that flows out from the filter element 5 to the inside seal part 13 that is a blood flow channel does not concentrate at one point (the outlet opening 11c) while passing through an extremely narrow gap where the outlet-side container 11 and the filter element 5 are adhered, but rather passes through a blood flow channel formed by the slit portions 7b and the like. Further, since at least one portion of the outlet opening 11c of the outlet port 11a is arranged so as to overlap at least one of the passage region S and the slit portions 7b, a state is entered in which the blood flow channel and the outlet port 11a are connected, and thus blood can be efficiently discharged to outside, and at the same time the risk of the outlet opening 11c being blocked by the filter element 5 can be eliminated.

Next, forms of the material and shape and the like of each element constituting the blood processing filter 1A are described. As described in the foregoing, the flexible container 3 is formed by the inlet-side container 9 and the outlet-side container 11. Any material that is commercially available as a sheet or a film can be used as a flexible resin that is used for the flexible container 3. For example, thermoplastic elastomers such as soft polyvinyl chloride, polyurethane, ethylene-vinyl acetate copolymer, polyolefin such as polyethylene and polypropylene, hydrogenated styrene-butadiene-styrene copolymer, styrene-isoprene-styrene copolymer, and hydrogenated products thereof, mixtures of the thermoplastic elastomer and a softening agent such as polyolefin and ethylene-ethyl acrylate; and the like may be mentioned as favorable materials. Since it can be considered that the material will contact with blood, preferable materials are soft polyvinyl chloride, polyurethane, and polyolefin that are used as the material of medical products such as blood bags, as well as thermoplastic elastomers containing these materials as main components, and more preferably the material is soft polyvinyl chloride.

Further, for example, a container described in Japanese Patent Laid-Open No. 7-267871 or a container described in International Publication No. WO 95/017236 can also be used as the flexible container 3.

The filter element 5 is manufactured using a filter material constituted by a fibrous integrated body such as nonwoven fabric or woven fabric or by a porous body such as sponge. The filter element 5 according to the present embodiment may be coated with a hydrophilic polymer to make it easier for blood to wet the filter material. Further, to facilitate attachment of leukocytes to the filter element 5 when using the blood processing filter 1A to remove leukocytes from blood, a filter material that is coated with a polymer may be used.

The flow channel securing sheet 7 can be manufactured using the same material as the flexible container 3, and the slit portions 7b can be appropriately manufactured by a punching process or other method. In this connection, according to the present embodiment, the slit portions 7b are exemplified as the flow channel holes 7b, and a form is described in which the two ends 7c thereof are arranged over the inner slanted face portion 6b of the valley part 6, and furthermore, the slit portions 7b are arranged in the passage region S formed by the valley part 6 when blood is flowing. However, the flow channel holes can take a variety of forms as long as one portion thereof is arranged in the passage region S. For example, with respect to a rectangular flow channel securing sheet 7 that is vertically long, the flow channel holes 7b may have a shape that is long in the vertical direction as in the present embodiment, or the flow channel holes may be long from side to side, or the flow channel holes may be a helical shape.

Further, according to the present embodiment, a form is described in which the plurality of flow channel holes 7b have substantially the same shape. However, the shapes and sizes of the plurality of flow channel holes need not necessarily be the same. For example, the flow channel holes may include both flow channel holes that are long in the vertical direction and flow channel holes that are long from side to side, and the width dimensions of the flow channel holes may be different to each other. Furthermore, flow channel holes of various shapes and dimensions may be arranged in an orderly arrangement or a random arrangement.

In addition, a configuration can be adopted in which a single flow channel hole is formed as a result of linking a plurality of slit-shaped holes to each other, and one portion thereof is linked to the outlet opening 11c. In particular, according to this configuration, a sufficient flow of blood can be secured even if a portion of the flow channel hole is not connected to the passage region S that is formed by the valley part 6 in a state in which blood is flowing. In this case, the fact that the slit-shaped holes are linked to each other means that sheet portions of the slit-shaped holes are in a cut state. Accordingly, the utmost care is required to ensure that the sheet portion of the flow channel securing sheet 7 does not break during the process of manufacturing the blood processing filter 1A. If that problem can be avoided, a function as the flow channel securing sheet 7 can be obtained.

Next, a method for manufacturing the blood processing filter 1A according to the present embodiment is described. According to this manufacturing method, for example, the inlet-side container 9 in which the inlet port 9a has been sealed at a predetermined position, the outlet-side container 11 in which the outlet port 11a has been sealed at a predetermined position, the filter element 5, and the flow channel securing sheet 7 are prepared, and an installing step is performed in which the inlet-side container 9 and the outlet-side container 11 are arranged so as to sandwich the filter element 5 and, further, the flow channel securing sheet 7 is arranged between the filter element 5 and the outlet-side container 11. In this case, the flow channel holes 7b through which blood that is processed by the filter element 5 passes are formed in the flow channel securing sheet 7, and the outlet port 11a is arranged at a predetermined position so as to be capable of communicating with the flow channel holes 7b.

Further, in the installing step, the flow channel securing sheet 7 is arranged at a predetermined position so that, when a state in which blood is flowing is assumed, at least one portion of the flow channel holes 7b formed in the flow channel securing sheet 7 is arranged in the empty space region (passage region) S that is formed by the valley part 6. In addition, the outlet opening 11c that communicates with the inside of the outlet-side container 11 is formed in the outlet port 11a, and at least one portion of the outlet opening 11c is arranged so as to overlap with at least one of the valley part 6 and the flow channel holes 7b.

Next, a sealing step is performed in which the inlet-side container 9 and the outlet-side container 11 are sealed in a state in which the inlet-side container 9 and the outlet-side container 11 sandwich the filter element 5 and the flow channel securing sheet 7 that have been arranged at predetermined positions in the installing step. The sealing step includes a first sealing step and a second sealing step. In the first sealing step, the inside seal part 13 is formed by sealing the inlet-side container 9, the filter element 5, and the flow channel securing sheet 7 in a band shape so as to surround the area in which the inlet port 9a is formed without adhering the filter element 5 and the outlet-side container 11. In the second sealing step, an annular outside seal part 15 is formed at a position that is closer to an outer edge than the inside seal part 13. The outside seal part 15 is formed by sealing so as to surround the inside seal part 13.

In the first sealing step, the valley part 6 that has a band shape that corresponds to the inside seal part 13 is generated on the outlet side of the filter element 5. In a state in which blood is flowing, the passage region S is formed between the outlet-side container 11 and the filter element 5 by the valley part 6.

Although formation of the inside seal part 13 in the first sealing step, more specifically, sealing of the inlet-side container 9, the filter element 5, and the flow channel securing sheet 7 can be performed utilizing high frequency welding, the present invention is not limited thereto, and any kind of bonding technique, such as ultrasonic welding or thermal welding, can be used. Preferably, the material used for the flow channel securing sheet 7 is the same as that used for the inlet-side container 9.

Likewise, although formation of the outside seal part 15 in the second sealing step, more specifically, sealing of the inlet-side container 9 and the outlet-side container 11 can be performed utilizing high frequency welding, the present invention is not limited thereto, and any kind of bonding technique, such as ultrasonic welding or thermal welding, can be used.

According to the above described manufacturing method, a form is described in which the inlet port 9a and the outlet port 11a are previously sealed to the flexible container 3. However, sealing may be performed after forming the inside seal part 13 or the outside seal part 15, or may be performed during the process of forming the inside seal part 13 or the outside seal part 15. Further, a method of sealing the inlet port 9a as a blood inlet and the outlet port 11a as a blood outlet to the flexible container 3 is not limited to high frequency welding, and any kind of bonding technique, such as thermal welding, can be used. Similarly to the flexible container 3, various known materials can be used as the material of the inlet port 9a and the outlet port 11a.

According to the above described manufacturing method, since the outlet-side container 11 is not included in the inside seal part 13, that is, since the outlet-side container 11 is not sealed to the filter element 5 and the flow channel securing sheet 7, there is the advantage that arrangement of the outlet port 11a in the step of sealing the outlet port 11a to the outlet-side container 11 can be performed with a comparatively high degree of freedom. More specifically, although sealing the inlet port 9a or the outlet port 11a inside the flexible container 3 is an advantage of the process of manufacturing the container welding type blood processing filter 1A in which forming the inside seal part 13 or the outside seal part 15 by a simple step is a feature, by adopting a configuration in which the inside seal part 13 does not seal the outlet-side container 11 it is possible to provide an even greater degree of freedom with respect to arrangement of the outlet port 11a. As a result, an optimal arrangement of elements in which the outlet port 11a overlaps with the flow channel holes 7b of the flow channel securing sheet 7 or the passage region S formed by the valley part 6 of the filter element 5 is facilitated.

Figure 7:
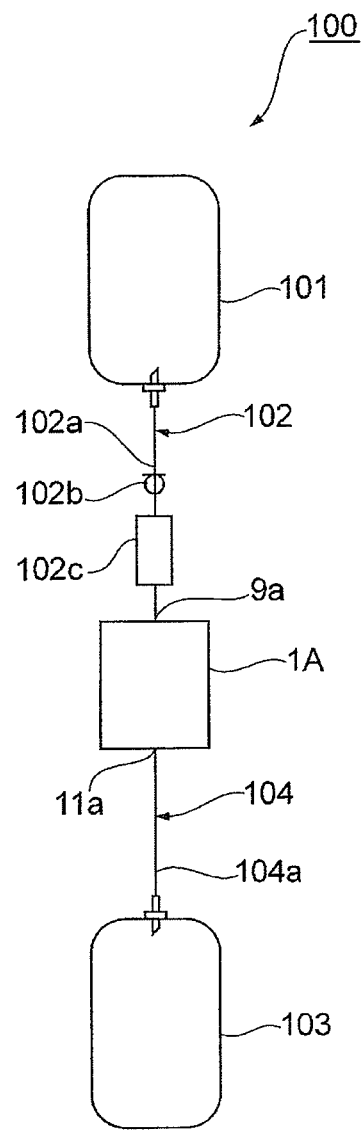
FIG. 7 is a front view that illustrates an outline of a blood processing system that includes a blood processing filter.
Figure 8:
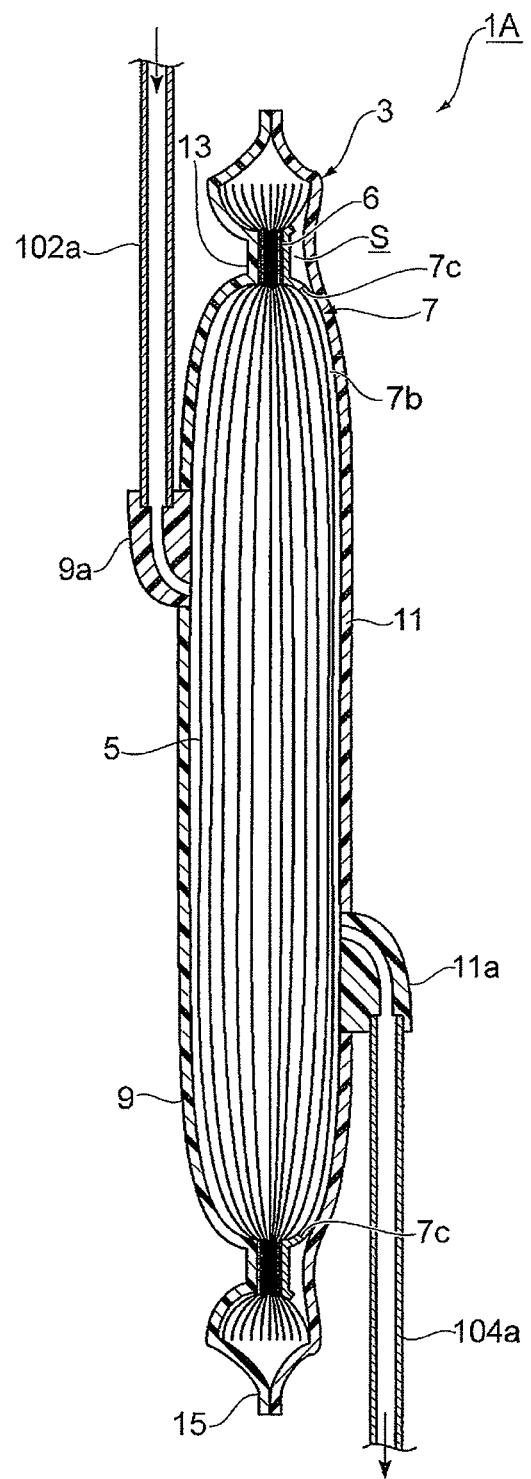
FIG. 8 is a sectional view that illustrates a state in which the blood processing filter is used.

Next, a blood processing system 100 that includes the blood processing filter 1A according to the first embodiment and a usage state (state in which blood is flowing) of the blood processing filter 1A is described referring to FIG. 7 and FIG. 8. FIG. 7 is a front view that illustrates an outline of a blood processing system. FIG. 8 is a sectional view that illustrates a state when the blood processing filter is being used.

The blood processing filter 1A can be used for filtering using gravity. For example, the blood processing system 100 to which the blood processing filter 1A is applied includes a reservoir bag 101 into which blood is filled after collection, the blood processing filter 1A, and a recovery bag 103 for accumulating blood after filtering. The reservoir bag 101 and the inlet port 9a of the blood processing filter 1A are connected to each other by a capillary tube 102a such as a blood tube. The recovery bag 103 and the outlet port 11a of the blood processing filter 1A are connected to each other by a capillary tube 104a such as a blood tube. Further, opening/closing means 102b such as a roller clamp that opens and closes a flow channel and a chamber 102c and the like is mounted in the capillary tube 102a on the upstream side. The inlet-side circuit 102 is formed by the capillary tube 102a, the opening/closing means 102b, and the chamber 102c and the like. The outlet-side circuit 104 is formed by the capillary tube 104a and the like on the downstream side.

The reservoir bag 101 into which blood is filled after collection is arranged at a position that is approximately 50 cm higher than the blood processing filter 1A. The recovery bag 103 in which blood is accumulated after filtering is arranged at a position that is approximately 100 cm lower than the blood processing filter 1A. A blood filtering process is performed by opening the flow channel of the blood processing system 100. When a filtering process is performed (at a time of use), a negative pressure arises on the outlet side of the flexible container 3 of the blood processing filter 1A, and the outlet-side container 11 deforms and attempts to adhere to the filter element 5. However, since the valley part 6 is formed on the outlet side of the filter element 5, and the recess 7a that is the same shape as the valley part 6 is also formed in the flow channel securing sheet 7, the passage region S that serves as a blood flow channel is formed between the filter element 5 and the outlet-side container 11 by the valley part 6 of the filter element 5 and the recess 7a of the flow channel securing sheet 7. Further, since one portion of the slit portions 7b of the flow channel securing sheet 7 is arranged in the passage region S, and the passage region S connects to the outlet port 11a, the blood flow channel from the slit portions 7b to the outlet port 11a is stably maintained without being blocked.

Next, the actions and effects of the blood processing filter 1A according to the present embodiment are described. According to the blood processing filter 1A, even if a dual force caused by a positive pressure on the inlet side and a negative pressure on the outlet side acts at the time of filtering, the flow of blood is ensured between the flow channel holes 7b of the flow channel securing sheet 7 and the outlet port 11a. Accordingly, it is possible to avoid a situation in which the flow of blood is inhibited by adherence or the like between the outlet-side container 11 and the filter element 5 of the blood processing filter 1A and filtering performance is lowered. This is advantageous in terms of effectively utilizing the entire filter element 5, and thus both a high filtering flow rate and high filtering performance can be achieved in a compatible manner.

Particularly, according to the blood processing filter 1A of the present embodiment, since at least one portion of the flow channel holes 7b formed in the flow channel securing sheet 7 is arranged over the inner slanted face portion 6b of the valley part 6, and is arranged in the passage region S formed by the valley part 6 in a state in which blood is flowing, all of the plurality of flow channel holes 7b are linked through the passage region S, and thus a drop in filtering performance accompanying blockage of the blood flow channel can be suppressed.

In addition, according to the blood processing filter 1A of the present embodiment, since at least one portion of the outlet opening 11c of the outlet port 11a is arranged so as to overlap with at least one of the passage region S and the flow channel holes 7b, after blood is processed by the filter element 5, the blood can be efficiently discharged to outside of the blood processing filter 1A, and at the same time the possibility that the outlet opening 11c will be blocked by the filter element 5 can also be avoided.

Further, according to the blood processing filter 1A of the present embodiment, the outlet-side container 11 is not included in the inside seal part 13. It is therefore possible to prevent a situation in which the filter element 5 in the vicinity of the inside seal part 13 is sandwiched by the flexible container 3 and the flow of blood is inhibited. Moreover, since the passage region S is formed by the valley part 6 corresponding to the inside seal part 13, and the passage region S can be utilized as a blood flow channel, it is possible to efficiently utilize the filter material at a peripheral portion of the filter element 5 in the vicinity of the inside seal part 13, at which, conventionally, blood tends to flow with difficulty.

Next, the advantages of the blood processing filter 1A and the method for manufacturing the blood processing filter 1A of the present embodiment are summarized. According to the blood processing filter 1A, the flow channel securing sheet 7 can be assembled inside the flexible container 3, and the flow channel holes 7b of the flow channel securing sheet 7 and the outlet port 11a can be connected and utilized as a blood flow channel without leading to the risk of a welding defect, complicating the manufacturing process, or increasing costs. As a result, a situation in which the flow of blood is inhibited and filtering performance declines can be avoided, more complete priming and air bleeding can be realized, the entire filter element 5 can be effectively utilized, and a high flow rate and high filtering performance can be simultaneously achieved. Further, the blood processing filter 1A that provides such advantages can be manufactured.

Figure 9:
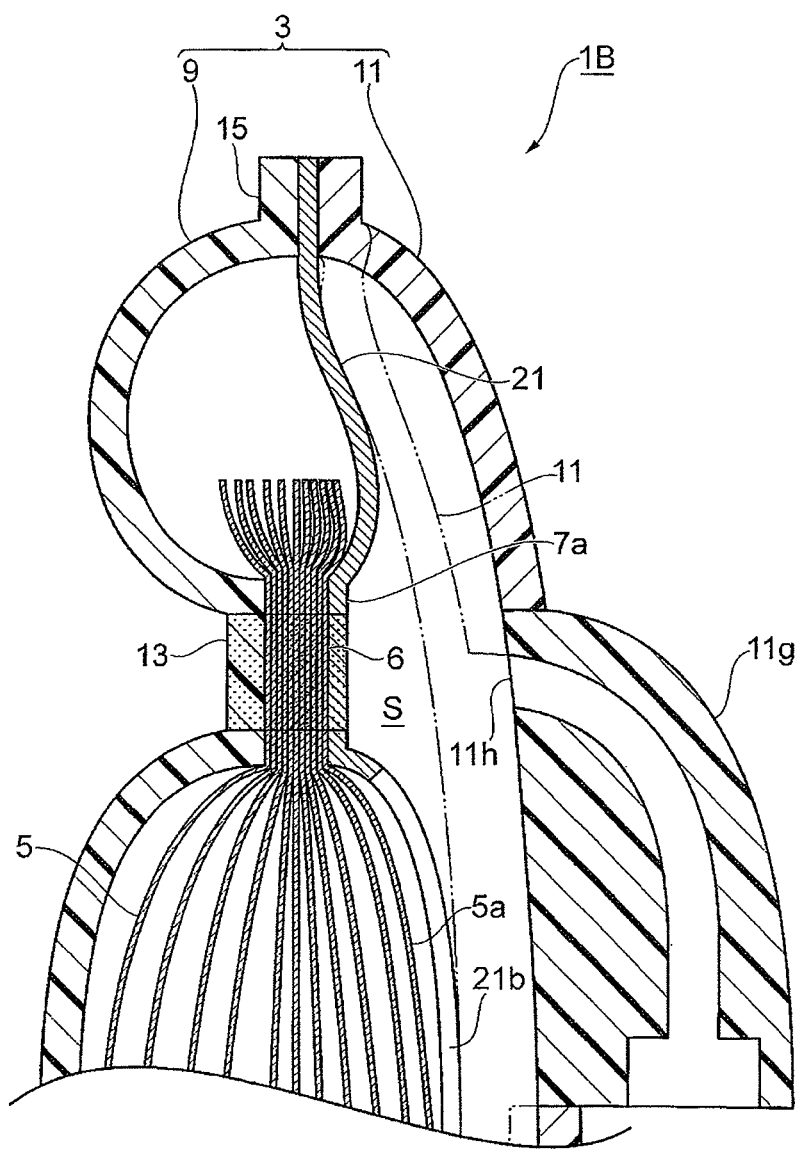
FIG. 9 is a sectional view that illustrates, in an enlarged manner, an end of a flow channel hole of a flow channel securing sheet and an inside seal part of a blood processing filter according to a second embodiment of the present invention.

Next, a blood processing filter according to a second embodiment of the present invention is described referring to FIG. 9. FIG. 9 is a sectional view that illustrates, in an enlarged manner, an end of a flow channel hole of a flow channel securing sheet and an inside seal part of a blood processing filter according to the second embodiment of the present invention. In this connection, in FIG. 9 an at-rest state is indicated by a solid line, and a state in which blood is flowing (a negative pressure state) is indicated by a chain double-dashed line. A blood processing filter 1B according to the second embodiment includes substantially the same elements and structures as the blood processing filter 1A according to the first embodiment. Hence, elements and structures that are the same as in the first embodiment are denoted by the same reference symbols and a detailed description thereof is omitted, and the following description centers on elements and structures that are different from those of the first embodiment.

The blood processing filter 1B includes a flexible container 3 that has an inlet port 9a and an outlet port 11a for blood, a sheet-like filter element 5 that is arranged so as to divide the inside of the flexible container 3 into an inlet port 9a side and an outlet port 11a side, and a flow channel securing sheet 21 that is arranged so as to overlap with the filter element 5. The flexible container 3 includes an inlet-side container 9 having a rectangular sheet shape, and an outlet-side container 11 having a rectangular sheet shape.

The inlet-side container 9 and the outlet-side container 11 overlap with each other through the rectangular filter element 5 and the rectangular flow channel securing sheet 21. The inlet-side container 9, the filter element 5, and the flow channel securing sheet 21 are sealed in close contact with each other, and as a result a band-shaped inside seal part 13 is formed along the periphery of the filter element 5.

The flow channel securing sheet 21 is arranged on the rear side of the filter element 5 so as to cover an effective filtering portion 5a of the filter element 5. A plurality of flow channel holes 21h are formed in a region facing the effective filtering portion 5a of the flow channel securing sheet 21, and at least one portion of all of the flow channel holes 21b is arranged over an inner slanted face portion 6b of a valley part 6. In a state in which blood is flowing, a passage region S is formed by the valley part 6 between the filter element 5 and the outlet-side container 11, and since one portion of the flow channel holes 21b is arranged in the passage region S, the flow channel holes 21b communicate with each other through the passage region S to thereby stably maintain the inflow and outflow of blood.

The area of the flow channel securing sheet 21 according to the present embodiment is wider than the area of the flow channel securing sheet 7 of the first embodiment. The flow channel securing sheet 21 is clamped and adhered between the periphery of the inlet-side container 9 and the periphery of the outlet-side container 11. That is, the inlet-side container 9, the flow channel securing sheet 21, and the outlet-side container 11 are sealed at a position that is closer to an outer edge than the inside seal part (first seal part) 13 to thereby form an outside seal part (second seal part) 15. Consequently, a sealing step of a method for manufacturing the blood processing filter 1B according to the present embodiment includes a first sealing step of sandwiching and adhering the filter element 5 between the inlet-side container 9 and the flow channel securing sheet 21, and a second sealing step of sandwiching and adhering the flow channel securing sheet 21 between the inlet-side container 9 and the outlet-side container 11.

Further, an outlet port 11g of the present embodiment is arranged at a position that is on an upper side of the blood processing filter 1B in a state in which the blood processing filter 1B is upright to perform blood processing, more specifically, at a position that is above the inlet port 9a when filtration is performed by means of a gravity drop, and in particular at a position in the vicinity of the passage region S that is the uppermost part thereof. At least one portion of the outlet opening 11h is arranged so as to overlap with the passage region S.

By adopting a configuration in which the outlet port 11g is arranged as described above, the blood processing filter 1B is filled with blood from the bottom upwards at a time of priming at the start of blood processing. As a result, since air can easily exit from the outlet port 11g that is arranged at the upper part of the blood processing filter 1B, more complete priming and air bleeding can be performed without the need to pay attention to a gravity drop setting or a flow rate at the time of priming. Thus, the filter element 5 can be utilized more effectively as a filter material, and a higher flow rate and higher filtering performance can be obtained. At such time, since the entire blood processing filter 1B swells because blood does not flow to outside the blood processing filter 1B until priming is completed, at first glance it seems that priming of the blood processing filter 1B requires time. However, in fact, after priming ends the blood accumulated on the outlet side is discharged to outside of the blood processing filter 1B at one time by the force of gravity, and since the filter material is utilized more effectively by the more complete priming, the overall time required for the entire blood processing can be shortened.

According to the blood processing filter 1B of the present embodiment, even if a dual force generated by a positive pressure on the inlet side and a negative pressure on the outlet side acts at the time of filtering, the flow of blood is ensured between the flow channel holes 21b of the flow channel securing sheet 21 and the outlet port 11g. Accordingly, it is possible to avoid a situation in which the blood flow is inhibited by adherence or the like between the outlet-side container 11 and the filter element 5 of the blood processing filter 1B and filtering performance is lowered. This is advantageous in terms of effectively utilizing the entire filter element 5, and thus both a high filtering flow rate and high filtering performance can be achieved in a compatible manner.

3According to the blood processing filter 1B, since the flow channel securing sheet 21 spreads so as to continue as far as the outside seal part 15, soakage of blood into the protruding nonwoven fabric portion 5c and loss of blood can be suppressed.

Figure 10:
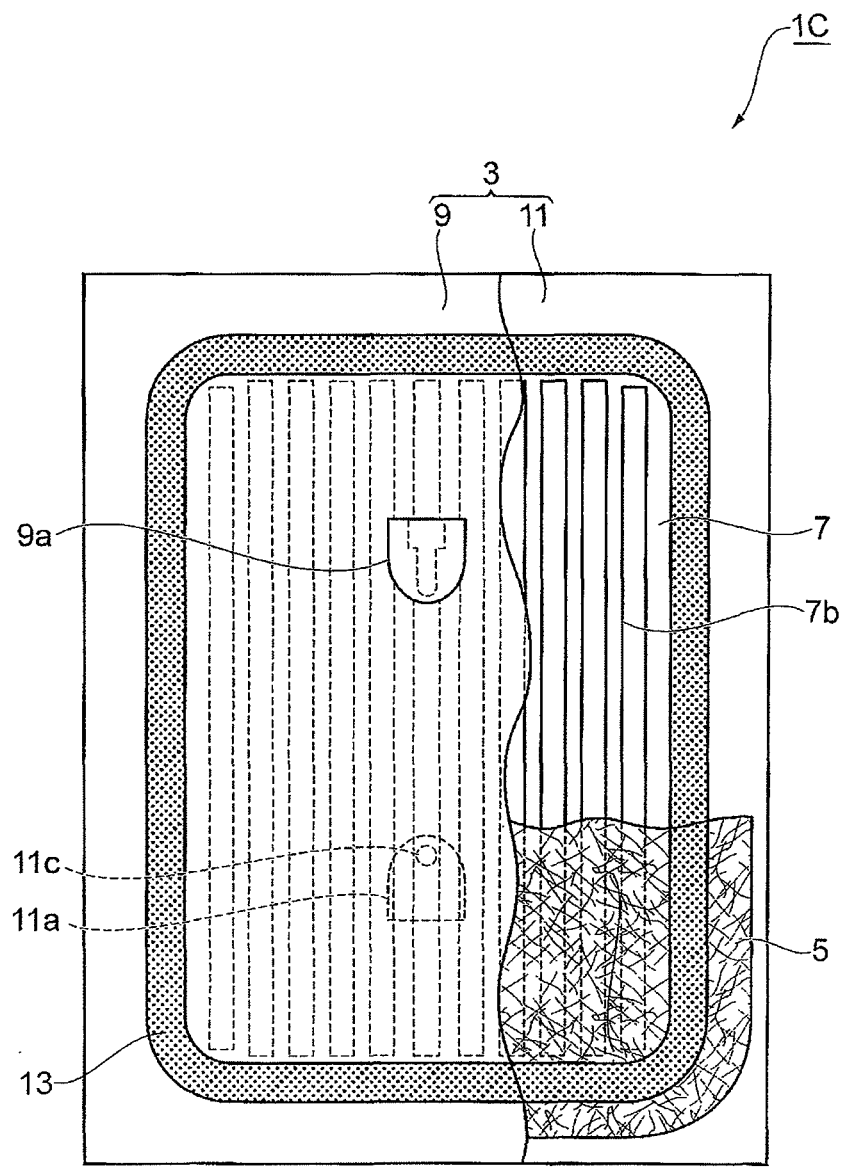
FIG. 10 is a plan view that illustrates one portion of a blood processing filter according to a third embodiment of the present invention, that is shown in a cut-away manner.

Next, a blood processing filter according to a third embodiment of the present invention is described referring to FIG. 10. FIG. 10 is a plan view that illustrates one portion of the blood processing filter according to the third embodiment, that is shown in cut-away manner. A blood processing filter 1C according to the third embodiment includes substantially the same elements and structures as the blood processing filter 1A according to the first embodiment. Hence, elements and structures that are the same as in the first embodiment are denoted by the same reference symbols and a detailed description thereof is omitted, and the following description centers on elements and structures that are different from those of the first embodiment.

In the blood processing filter 1C according to the present embodiment, an outside seal part is not formed, and only an inside seal part 13 that clamps a filter element 5 and a flow channel securing sheet 7 in a rectangular ring shape is formed between an inlet-side container 9 and an outlet-side container 11. In the inlet-side container 9, an inlet port 9a is sealed in a region that is surrounded by the inside seal part 13. In the outlet-side container 11, an outlet port 11a is sealed in a region that is surrounded by the inside seal part 13. At least one portion of an outlet opening 11c of the outlet port 11a is arranged so as to overlap with flow channel holes 7b of the flow channel securing sheet 7, and thus a form in which the outlet port 11a is capable of communicating with the flow channel holes 7b is realized. According to the present embodiment, since the flow channel holes 7b and the outlet opening 11c are connected as a blood flow channel, it is possible to avoid a situation in which the flow of blood is inhibited by adherence or the like between the outlet-side container 11 and the filter element 5 and filtering performance is lowered. This is advantageous in terms of effectively utilizing the entire filter element 5, and thus both a high filtering flow rate and high filtering performance can be achieved in a compatible manner.

Figure 11:
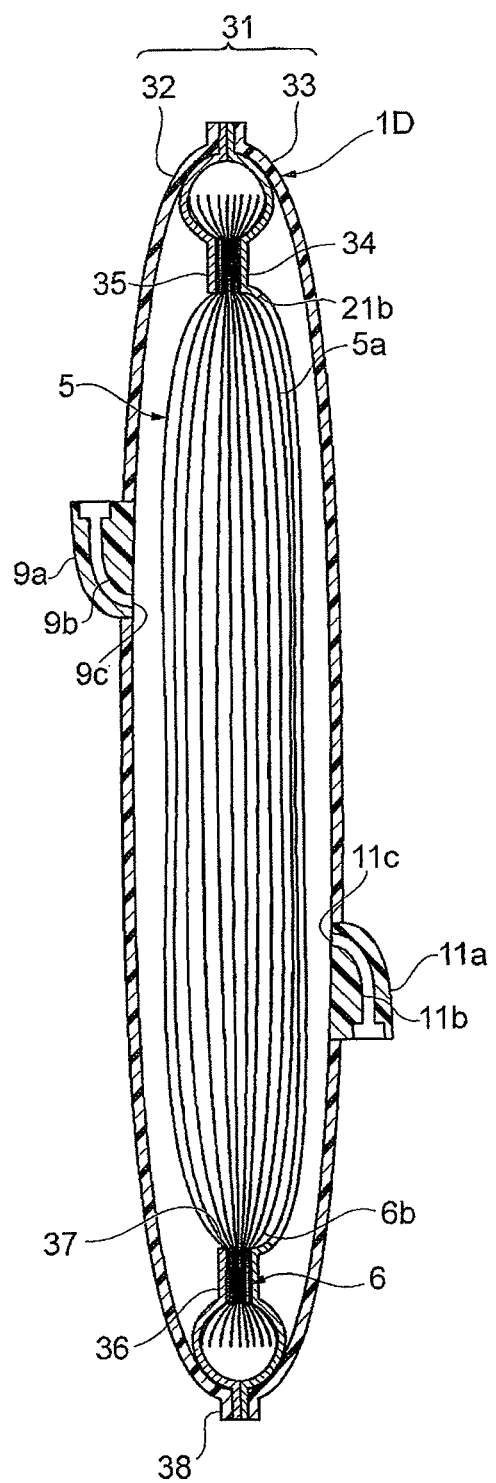
FIG. 11 is a sectional view of a blood processing filter according to a fourth embodiment of the present invention.

Next, a blood processing filter according to a fourth embodiment of the present invention is described referring to FIG. 11. FIG. 11 is a sectional view of the blood processing filter according to the fourth embodiment, which shows the blood processing filter in an at-rest state. A blood processing filter 1D according to the fourth embodiment includes substantially the same elements and structures as the blood processing filter 1A according to the first embodiment and the blood processing filter 1B according to the second embodiment. Hence, elements and structures that are the same as in the first or second embodiment are denoted by the same reference symbols and a detailed description thereof is omitted, and the following description centers on elements and structures that are different from those of the first or second embodiment.

The blood processing filter 1D includes a flexible container 31 having an inlet port 9a and an outlet port 11a for blood, a sheet-like filter element 5 that is arranged so as to divide the inside of the flexible container 31 into an inlet port 9a side and an outlet port 11a side, a flow channel securing sheet 34 that is arranged so as to overlap with the filter element 5 on the outlet side of the filter element 5, and a welding frame sheet 35 that is arranged so as to overlap with the filter element 5 on the inlet side of the filter element 5. The flexible container 31 includes an inlet-side container 32 having a rectangular sheet shape, and an outlet-side container 33 having a rectangular sheet shape.

The welding frame sheet 35 and the flow channel securing sheet 34 overlap with each other so as to sandwich the rectangular filter element 5. The welding frame sheet 35 and the flow channel securing sheet 34 clamp the filter element 5 along the periphery of the filter element 5. The area at which the filter element 5 is clamped is sealed in a band shape to form an annular inside seal part (first seal part) 36. That is, according to the present embodiment, instead of the inlet-side container 32, the welding frame sheet 35 is welded to and integrated with the filter element 5 and the flow channel securing sheet 34, and as a result the inside seal part 36 is formed. Further, according to the present embodiment, a valley part 6 is formed on the outlet side of the filter element 5 by the inside seal part 36.

In the welding frame sheet 35, a rectangular opening 37 that exposes a surface on the inlet side of the filter element 5 is formed on an inner side that is surrounded by the inside seal part 36. In this connection, although in the welding frame sheet 35 according to the present embodiment a single opening 37 is provided in a shape that is formed by cutting out all of the inner side that is surrounded by the inside seal part 36, a configuration may also be adopted in which one or a plurality of openings are formed by adopting a shape in which one portion of the inner side that is surrounded by the inside seal part 36 remains.

The inlet-side container 32 and the outlet-side container 33 overlap with each other through the welding frame sheet 35, the filter element 5, and the flow channel securing sheet 34. The peripheries of the inlet-side container 32 and the outlet-side container 33 overlap with the peripheries of the welding frame sheet 35 and the flow channel securing sheet 34 and are sealed in a band shape to thereby form an annular outside seal part (second seal part) 38.

According to the present embodiment, the peripheries of the welding frame sheet 35 and the flow channel securing sheet 34 are clamped by the inlet-side container 32 and the outlet-side container 33, and are sealed and integrated. However, the welding frame sheet 35 may be a small size that is of a degree that enables the formation of the inside seal part 36. Further, the flow channel securing sheet 34 and the welding frame sheet 35 can be manufactured using the same material as the flexible container 3.

Similarly to the flow channel securing sheet 21 according to the second embodiment, a plurality of flow channel holes 21b are formed in the flow channel securing sheet 34, and at least one portion of all of the flow channel holes 21b is arranged over an inner slanted face portion 6b of the valley part 6. In a state in which blood is flowing, a passage region (empty space region) S is formed by the valley part 6 between the filter element 5 and the outlet-side container 33, and since one portion of the flow channel holes 21b is arranged inside the passage region S, the flow channel holes 21b communicate with each other through the passage region S so that the inflow and outflow of blood are stably maintained.

According to the blood processing filter 1D of the present embodiment, even if a dual force generated by a positive pressure on the inlet side and a negative pressure on the outlet side acts at the time of filtering, the flow of blood is ensured between the flow channel holes 21b of the flow channel securing sheet 34 and the outlet port 11a. Accordingly, it is possible to avoid a situation in which the flow of blood is inhibited by adherence or the like between the outlet-side container 33 and the filter element 5 of the blood processing filter 1D and filtering performance is lowered. This is advantageous in terms of effectively utilizing the entire filter element 5, and thus both a high filtering flow rate and high filtering performance can be achieved in a compatible manner.

EXAMPLES

The present invention will now be described in further detail below by way of examples. However, the following examples should not be construed as limiting the present invention.

Example 1

A filter including an inlet-side container (inlet-side flexible container), an outlet-side container (outlet-side flexible container), a filter element and a flow channel securing sheet was prepared, and an inlet port thereof was connected to a pre-filtration liquid reservoir bag via an inlet-side circuit having a length of 50 cm. An outlet port of the filter was connected to a post-filtration liquid recovery bag via an outlet-side circuit having a length of 100 cm. A tube made of soft polyvinyl chloride having an internal diameter of 2.9 mm and an external diameter of 4.2 mm was used for the inlet-side circuit and the outlet-side circuit.

In preparing the filter, an effective filtering portion was formed in a rectangular shape in which an inner side of an inside seal part (first seal part) had a longitudinal dimension of 74 cm and a horizontal dimension of 57 cm, a corner portion was formed as a curve, and an effective filtration area of $42 \times 10^{-4}$ ($m^2$) was provided. As the filter element, four sheets of polyester nonwoven fabric having an air permeability of 237.3 ($cc/cm^2/sec$) and a thickness of 0.2 mm, one sheet of polyester nonwoven fabric having an air permeability of 8.4 ($cc/cm^2/sec$) and a thickness of 0.4 mm, 32 sheets of polyester nonwoven fabric having an air permeability of 7.7 ($cc/cm^2/sec$) and a thickness of 0.20 mm, one sheet of nonwoven polyester fabric having an air permeability of 8.4 ($cc/cm^2/sec$) and a thickness of 0.4 mm, and four sheets of nonwoven polyester fabric having an air permeability of 237.3 ($cc/cm^2/sec$) and a thickness of 0.2 mm were stacked in that order from an inlet to an outlet at the time of filtering blood, and used. In this connection, the air permeability was measured by a method based on Japanese Industrial Standard JIS L-1096, 6.27.1A. The flow channel securing sheet was sealed at the same time as the first seal part was formed. The size of flow channel securing sheet was made larger than the entire external side of the first seal part and smaller than the laminated filter element. Similarly to the flexible container, a flexible sheet having a thickness of 0.4 mm was used for the flow channel securing sheet, and 11 slit portions with a length of 72 mm and a width of 3 mm were formed at portions that were further on the inside than the first seal part by cutting out the sheet. At that time, the slit portions were formed such that the positions thereof in the vertical direction were aligned and intervals between the slit portions in the width direction were 2 mm, so that the slit portions were symmetrical when viewed from the center of the first seal part.

The inlet port and the outlet port were sealed to the inlet-side flexible container and the outlet-side flexible container, respectively. The outside seal part (first seal part) was formed by disposing the inlet-side flexible container and the flow channel securing sheet in a layered arrangement so as to sandwich the filter element therebetween, and thereafter the second seal part was formed by overlaying the outlet-side flexible container on the opposite side of the inlet-side flexible container. At that time, sealing and assembly were performed so as to provide an inlet opening for allowing blood to flow out from the inlet port to inside the flexible container at a position that was 2.4 cm below an end on the effective filtering portion side of the uppermost portion of the first seal part. Further, sealing and assembly were performed so as to provide an outlet opening for allowing blood processed by the filter element to flow out to an outlet flow channel inside the outlet port at a position that was 2.4 cm above an end on the effective filtering portion side of the lowermost portion of the first seal part. Assembly was performed so as to arrange the outlet opening of the outlet port in the center in the width direction of the inner side of the first seal part, and so that one portion of the outlet opening overlapped with a central slit portion among the plurality of slit portions of the flow channel securing sheet.

The total of the upstream side drop, the drop between the inlet and outlet of the blood processing filter, and the downstream side drop was fixed at 150 cm. Thereafter, as a liquid to be processed (a blood substitute), 300 g of an aqueous solution of polyvinyl pyrrolidone (molecular weight: 360,000) adjusted to a viscosity of 17 mPa·s (25° C.) and pH 3.8 was filled into a pre-filtration liquid reservoir bag, and caused to flow at room temperature using gravity. A post-filtration liquid recovery bag was placed in advance on a scale balance to enable verification of changes in the weight thereof.

At this time, the time required from when the liquid to be processed started to flow until the liquid first reached the inlet of the post-filtration liquid recovery bag was measured, and the measured time was defined as a priming time (minutes). Further, a time required from when the liquid to be processed started to flow until all of the liquid to be processed was discharged from inside the pre-filtration liquid reservoir bag and a converted weight of the post-filtration liquid recovery bag ceased to increase, more specifically, the time required to filter all of the liquid, was measured, and the measured time was defined as a total processing time (minutes). The weight of the liquid recovered in the post-filtration liquid recovery bag was measured and defined as a recovery amount (g). A mean processing speed (g/min) was determined by calculation based on the recovery amount and the total processing time. A difference between the 300 g of liquid that was filled into the pre-filtration liquid reservoir bag and the recovery amount was determined by calculation, and defined as a loss amount (g).

Example 2

Filtering was carried out using a filter assembled by the same method as in Example 1, except that the periphery of the flow channel securing sheet continued as far as the second seal part, and the second seal part was formed by sealing the inlet-side flexible container, the flow channel securing sheet, and the outlet-side flexible container.

Example 3

Filtering was carried out using a filter assembled by the same method as in Example 2, except that sealing and assembly were performed such that an outlet opening for allowing liquid to flow out from inside the flexible container to an outlet port overlapped with a lowermost portion of the first seal part (lowermost portion of a passage region formed by a valley part corresponding to the first seal part in a state in which blood is flowing).

Example 4

Filtering was carried out using a filter assembled by the same method as in Example 2, except that sealing and assembly were performed such that an outlet opening for allowing liquid to flow out from inside the flexible container to an outlet port overlapped with an uppermost portion of the first seal part (uppermost portion of a passage region formed by a valley part corresponding to the first seal part in a state in which blood is flowing).

Example 5

Filtering was carried out using a filter assembled by the same method as in Example 2, except that a flow channel securing sheet having a thickness of 0.8 mm was used.

Example 6

Filtering was carried out using a filter assembled by the same method as in Example 2, except that a first seal part was formed by disposing a welding frame sheet and the flow channel securing sheet in a layered arrangement so as to sandwich the filter element therebetween, thereafter the outlet-side flexible container was overlaid on the flow channel securing sheet side, and the inlet-side flexible container was overlaid on the welding frame sheet side to thereby form a second seal part by clamping and sealing both the flow channel securing sheet and the welding frame sheet between the outlet-side flexible container and the inlet-side flexible container.

Comparative Example 1

Filtering was carried out using a filter assembled by the same method as in Example 1, except that a flow channel securing sheet was not used.

Comparative Example 2

Filtering was carried out using a filter assembled by the same method as in Comparative Example 1, except that a first seal part was formed by disposing the inlet-side flexible container, the filter element, and the outlet-side container in a layered arrangement, and thereafter the second seal part was formed.

Table 1 shows a summary of the results of Examples 1 to 6, and Comparative Examples 1 and 2.

In Example 1, the total processing time is shortened and the mean processing speed is improved compared to Comparative Example 1. This is because, as a result of using the flow channel securing sheet in Example 1, filter material at a distant position from the outlet port is also effectively utilized and a situation does not arise in which the outlet opening of the outlet port contacts the filter material and is blocked. More specifically, liquid that flowed out from various areas in a planar direction did not concentrate at one point of the outlet port, but rather flowed in diffuse directions through the slit portions of the flow channel securing sheet, passed through the passage region corresponding to the first seal part as a flow channel, flowed again into the slit portions connected to the outlet opening of the outlet port, and was discharged to outside the filter through the outlet port.

According to Example 2, the flow channel securing sheet continues as far as the second seal part. Consequently, there is no soakage to the protruding nonwoven fabric portion or loss of liquid. The loss amount according to Example 2 is substantially equal to Comparative Example 2. Due to the effect of the slit portions of the flow channel securing sheet, a decrease in the priming time and total processing time was observed in comparison to Comparative Example 2, and a processing speed equivalent to that of Example 1 was obtained.

According to Example 3, the outlet opening of the outlet port is arranged so as to overlap with the lowermost portion of the first seal part. Since the slit portions of the flow channel securing sheet and the passage region are connected, and the effect is substantially the same whether the outlet port is overlapping with the slit portions or the passage region, the results for time and speed were approximately equal in Example 3 and Example 2.

Although the structure of Example 4 is equivalent to that of Example 3, the outlet opening of the outlet port is arranged so as to overlap with the uppermost portion of the first seal part. Therefore, it is found that the priming time is longer than in Example 3. However, this is not a substantial extension of the priming time, but rather relates to the fact that the outlet port is disposed at the upper portion of the filter in order to carry out more complete priming and air bleeding. More specifically, it is because only air is discharged and liquid is not discharged to outside the filter during priming, and hence the outlet side of the filter is filled with liquid. Once liquid starts to flow out from the filter and the outlet-side circuit is filled with liquid, the liquid accumulated on the outlet side of the filter is rapidly discharged to outside the filter by a negative pressure. Accordingly, a mean processing speed that was the same level as that of Example 3 was obtained without the apparent extension in the priming time extending the total processing time.

TABLE 1

|  | Example 1 | Example 2 | Example 3 | Example 4 | Example 5 | Example 6 | Comparative Example 1 | Comparative Example 2 |
|---|---|---|---|---|---|---|---|---|
| Priming Time (min) | 2.8 | 2.0 | 2.1 | 2.6 | 2.1 | 2.1 | 2.8 | 2.3 |
| Total Processing Time (min) | 17.3 | 17.6 | 17.5 | 17.1 | 16.0 | 17.8 | 26.1 | 26.4 |
| Recovery amount (g) | 257.9 | 260.2.8 | 259.9 | 259.3 | 258.4 | 260.0 | 258.3 | 260.9 |
| Mean Processing Speed (g/min) | 14.9 | 14.5 | 14.9 | 15.2 | 16.2 | 14.6 | 9.9 | 9.9 |
| Loss Amount (g) | 42.1 | 39.8 | 40.1 | 40.7 | 41.6 | 40.0 | 41.7 | 39.1 |

According to Example 5, although the blood processing filter is assembled in the same way as in Example 2, the thickness of the flow channel securing sheet that is used is 0.8 mm, which is twice the thickness of the flow channel securing sheet used in Example 2. As a result, although a certain increase in the loss amount was observed, the effect produced by the slit portions of the flow channel securing sheet increased, and a higher mean processing speed was obtained.

According to Example 6, the first seal part is formed so as to sandwich the filter element with the welding frame sheet instead of the inlet-side flexible container. A mean processing speed of the same level as that of Example 2 was obtained.

What is claimed is:

1. A blood processing filter comprising a sheet-like filter element, an inlet-side flexible container and an outlet-side flexible container that sandwich the filter element and are sealed thereto, an inlet port provided in the inlet-side flexible container for accepting blood before being processed by the filter element, and an outlet port provided in the outlet-side flexible container for discharging blood after being processed by the filter element;
    further comprising a flow channel securing sheet that is arranged between the filter element and the outlet-side flexible container;
    a first seal part that seals the inlet-side flexible container and the filter element in a band shape, and that is provided so as to surround the inlet port; and
    an annular second seal part that seals at least the inlet-side flexible container and the outlet-side flexible container, and that is provided so as to surround the first seal part at a position that is closer to an outer edge than the first seal part;
    wherein:
    a flow channel hole through which blood that is processed by the filter element passes is formed in the flow channel securing sheet; and
    the outlet port is provided so as to be capable of communicating with the flow channel hole; and
    a valley part corresponding to the first seal part is provided on an outlet side of the filter element, and at least one portion of the flow channel hole that is formed in the flow channel securing sheet is arranged in an empty space region that is formed by the valley part in a state in which blood is flowing.

2. The blood processing filter according to claim 1, wherein: the flow channel hole comprises a plurality of flow channel holes formed in the flow channel securing sheet; and at least one portion of all of the flow channel holes is arranged in the empty space region that is formed by the valley part.

3. The blood processing filter according to claim 1, wherein an outlet opening that communicates with an inside of the outlet-side flexible container is formed in the outlet port, and at least one portion of the outlet opening is arranged so as to overlap with at least one of the flow channel hole and the valley part.

4. The blood processing filter according to claim 1, wherein the second seal part sandwiches and adheres the flow channel securing sheet between the inlet-side flexible container and the outlet-side flexible container.

5. The blood processing filter according to claim 1, wherein the first seal part sandwiches and adheres the filter element between the inlet-side flexible container and the flow channel securing sheet.

6. The blood processing filter according to claim 1, wherein:
    the second seal part sandwiches and adheres the flow channel securing sheet between the inlet-side flexible container and the outlet-side flexible container; and
    the first seal part sandwiches and adheres the filter element between the inlet-side flexible container and the flow channel securing sheet.

7. The blood processing filter according to claim 1, wherein: the flow channel securing sheet is arranged so as to cover an effective filtering portion of the filter element; and the flow channel hole comprises a plurality of flow channel holes formed in the flow channel securing sheet in a region that faces the effective filtering portion.

8. The blood processing filter according to claim 7, wherein, in the flow channel securing sheet, a proportion of a gross area of the flow channel holes with respect to an area of the effective filtering portion is between 30% and 99%.

* * * * *